USO05575901A

United States Patent [19]

Hulme et al.

[11] Patent Number: 5,575,901
[45] Date of Patent: Nov. 19, 1996

[54] PROCESS FOR PREPARING ORGANIC AND INORGANIC HYDROXIDES OR ALKOXIDES OR AMMONIA OR ORGANIC AMINES FROM THE CORRESPONDING SALTS BY ELECTROLYSIS

[75] Inventors: David R. Hulme; Hossein Sharifian, both of Austin, Tex.

[73] Assignee: Sachem, Inc., Austin, Tex.

[21] Appl. No.: 381,318

[22] Filed: Jan. 31, 1995

[51] Int. Cl.$^6$ .............................. C02F 1/46; B01D 61/44
[52] U.S. Cl. .................. 205/413; 205/508; 205/538; 205/551; 205/552; 204/522; 204/523; 204/541; 204/544
[58] Field of Search ................................ 204/96, 98, 100, 204/102, 103, 182.4, 522, 523, 541, 544; 205/413, 508, 538, 551, 552

[56] References Cited

U.S. PATENT DOCUMENTS

| Re. 32,398 | 4/1987 | De Witt et al. ............................ 204/72 |
| 3,402,115 | 9/1968 | Campbell et al. ...................... 204/180 |
| 4,521,285 | 6/1985 | Buonomo et al. ...................... 204/102 |
| 4,572,769 | 2/1986 | Shimizu ................................. 204/59 R |
| 4,578,161 | 3/1986 | De Witt et al. ............................ 204/72 |
| 5,286,354 | 2/1994 | Bard et al. ................................ 204/86 |
| 5,389,211 | 2/1995 | Sharifian et al. ........................ 204/72 |

FOREIGN PATENT DOCUMENTS

| 0420311 | 4/1991 | European Pat. Off. . |
| 60-131985 | 7/1985 | Japan . |
| 60-131986 | 7/1985 | Japan . |
| 2129390 | 5/1990 | Japan . |

OTHER PUBLICATIONS

Gomez et al, "Electrosynthesis of Quaternary Ammonium Hyperoxides", Journal of Applied Electrochemistry 21 (1991), p. 365–367.

Primary Examiner—Arun S. Phasge
Attorney, Agent, or Firm—Renner, Otto, Boisselle & Sklar

[57] ABSTRACT

A process is described for preparing organic and inorganic hydroxides or alkoxides, or ammonia or organic amines from the corresponding salts in an electrolysis cell which comprises an anolyte compartment containing an anode and an electrolyte solution, a catholyte compartment containing a cathode, and an intermediate compartment containing a liquid wherein said intermediate compartment is separated from the catholyte compartment by an anion selective membrane and from the anolyte compartment by a cation selective membrane, said process comprising the steps of:

(A) charging to the catholyte compartment, a mixture comprising an organic or inorganic salt or an amine salt, and a liquid selected from water or organic liquids provided that sufficient water is present in the catholyte mixture to form the desired hydroxide or amine, or sufficient alcohol is present in the catholyte mixture to form the desired alkoxide;

(B) passing a current through the electrolysis cell to produce the desired hydroxide, alkoxide or amine in the catholyte compartment and an acid in the intermediate compartment;

(D) recovering the organic or inorganic hydroxide or alkoxide or the amine from the catholyte compartment; and (E) recovering the acid from the intermediate compartment.

The organic and inorganic hydroxides and alkoxides, or amines prepared by the process of the invention are characterized by improved purity, and production costs are lower than many other processes. The processes of the invention also are particularly useful for preparing higher molecular weight quaternary and tertiary ammonium hydroxides and alkoxides.

29 Claims, 1 Drawing Sheet

PROCESS FOR PREPARING ORGANIC AND INORGANIC HYDROXIDES OR ALKOXIDES OR AMMONIA OR ORGANIC AMINES FROM THE CORRESPONDING SALTS BY ELECTROLYSIS

FIELD OF THE INVENTION

This invention relates to a method for preparing organic and inorganic hydroxides or alkoxides or amines from the corresponding salts by electrolysis. The invention also relates to the high purity hydroxides obtained by the process of the invention.

BACKGROUND OF THE INVENTION

Quaternary ammonium hydroxides such as tetramethylammonium hydroxide (TMAH) and tetraethyl ammonium hydroxide CTEAH) are strong organic bases that have been known for many years. Such quaternary ammonium hydroxides have found a variety of uses including use as titrants for acids in organic solvents and as supporting electrolytes in polarography. Aqueous solutions of quaternary ammonium hydroxides, particularly TMAH solutions, have been used extensively as a developer for photoresists in printed circuit board and microelectronic chip fabrication. Use of quaternary ammonium hydroxides in the electronics area requires that there be no residue following the normal post-bake period. In electronic applications, it is desirable that the aqueous solutions of quaternary ammonium hydroxides should be essentially free from metal ions such as sodium, potassium, zinc and calcium; anions such as halides, nitrates, nitrites, carbonates, carboxylates, sulfates and neutral organic species such as methanol, amines, etc. Particularly in recent years, there has been an increasing demand for quaternary ammonium hydroxides having a high purity.

Quaternary ammonium hydroxides also are useful as reagents for removing hydrohalide impurities from quaternary ammonium salt reaction products thereby providing metal-free, hydrohalide-free quaternary ammonium salts; as intermediates for synthesizing quaternary ammonium salts by neutralization with appropriate acids; as solubilizers for anions in organic solutions (e.g., phase transfer catalysts); as templating agents for zeolites; as supporting electrolytes in electroorganic synthesis and electroanalysis; as cleaning agents for electronic circuits; and as strong base catalysts.

A number of prior art patents describe the preparation of quaternary ammonium hydroxides by electrolyzing a salt of a quaternary ammonium compound. U.S. Pat. Redesign 32,398 (DeWitt et at) describes an electrolytic process for removing the anion from quaternary organic salts. The process uses a cell comprising four compartments containing two cation exchange membranes defining the cathode and anode compartments and an anion exchange membrane dividing the space between the two cation exchange membranes into two inner compartments. The quaternary organic salt is charged to the inner compartment which is adjacent to the catholyte compartment and is thus separated from the catholyte compartment by the cation exchange membrane. Water is charged to the other three compartments and a small amount of an electrolyte is also charged to the anolyte compartment. On passage of a current, the quaternary cation passes through the cation exchange membrane into the catholyte compartment and a hydroxide ion is formed resulting in the formation of a quaternary hydroxide in the catholyte compartment. The anion of the salt passes through the anion exchange resin into the inner compartment which is adjacent to the catholyte anolyte compartment. In this process, the quaternary organic hydroxide is recovered from the catholyte compartment and an inorganic acid is recovered from the inner compartment adjacent to the anolyte compartment.

U.S. Pat. No. 3,402,115 (Campbell et al) describe the preparation of quaternary ammonium hydroxides from a bis-quaternary ammonium sulfate in an electrolytic cell containing three chambers. The three chambers include an anolyte chamber containing an anode, a catholyte chamber containing a cathode, and a chamber containing a bis-quaternary ammonium sulfate salt positioned between the anolyte and catholyte chambers. The salt containing chamber is separated from the anolyte chamber by an anion exchange resin membrane, and is separated from the catholyte chamber by a cation exchange resin membrane. An aqueous sulfuric acid solution is continuously circulated through the anolyte chamber, and a dilute aqueous quaternary ammonium hydroxide solution is continuously circulated through the catholyte chamber. When an electric potential is applied, sulfate ions migrate through the anion exchange membrane into the anolyte chamber, and quaternary ammonium ions migrate through the cation exchange membrane into the catholyte chamber. The quaternary ammonium hydroxide product is obtained by withdrawing a portion of the aqueous solution from the catholyte chamber.

U.S. Pat. No. 5,286,354 (Bard et al) describe a method of preparing organic and inorganic hydroxides and alkoxides from the corresponding halide salts in a two-compartment divided cell. The desired compounds are formed in the catholyte while the accumulation of halogen in the anolyte is effectively prevented through the action of a reducing agent added to the acidic anolyte solution.

Copending application Ser. No. 08/148,925, filed Nov. 8, 1993, describes the process for preparing organic and inorganic hydroxides or alkoxides and for improving the purity of organic and inorganic hydroxides or alkoxides utilizing a three-compartment electrolysis cell. The electrolysis cell comprises an anolyte compartment containing an anode, a catholyte compartment containing a cathode in water, and at least one intermediate compartment containing water, an organic liquid, or a mixture of water and an organic liquid, said at least one intermediate compartment being separated from the anolyte and catholyte compartments by at least two dividers selected from nonionic dividers, cation selected membranes, or combinations thereof. A mixture comprising an organic or inorganic hydroxide and an oxidizable liquid is charged to the anolyte compartment and a current is passed through the electrolysis cell to produce the purified organic or inorganic hydroxide in the catholyte compartment which is then recovered from the catholyte compartment.

Japanese Kokai Patent No. 60-131985 (1985) Crakahashi et at) describes a method of manufacturing a high purity quaternary ammonium hydroxide in an electrolysis cell which is divided into an anode chamber and a cathode chamber by a cation exchange membrane. A quaternary ammonium hydroxide solution containing impurities is charged to the anode chamber and a direct current is supplied between two electrodes after water has been charged to the cathode chamber. Purified quaternary ammonium hydroxide is obtained from the cathode chamber. The purified quaternary ammonium hydroxide contains reduced amounts of alkali metals, alkaline earth metals, anions, etc.

Japanese Kokai Patent No. 60-131986 (1985) Crakahashi et al) describes a method for manufacturing a high purity quaternary ammonium hydroxide. The method described in this patent utilizes an electrolysis cell which has been compartmentalized into an anode chamber, a cathode chamber, and at least one intermediate chamber with at least two cation exchange membranes. An aqueous solution containing a quaternary ammonium salt is charged to the anode chamber, water is charged to the cathode chamber, and an aqueous hydroxide solution corresponding to the quaternary ammonium salt charged into the anode chamber is charged into the intermediate chamber. Upon application of a direct current, a quaternary ammonium hydroxide is formed in the cathode chamber and recovered.

Japanese Kokai Patent No. Hei 2[11990]129390 describes a method of preparing quaternary ammonium hydroxide from a quaternary ammonium salt. The method described in this patent utilizes an electrolysis cell which has been compartmentalized into an anode chamber, a cathode chamber and an intermediate chamber. The intermediate chamber is separated from the cathode chamber by a cation exchange membrane, and the intermediate compartment is separated from the anolyte compartment by an anion exchange membrane. An aqueous solution containing a quaternary ammonium salt is charged to the intermediate chamber and water is charged to the cathode and anode chambers. Upon application of a direct current, quaternary ammonium hydroxide is formed in the cathode compartment and recovered. An acid is formed in the anode compartment.

SUMMARY OF THE INVENTION

A process is described for preparing organic and inorganic hydroxides or alkoxides, or ammonia and organic amines from the corresponding salts in an electrolysis cell which comprises an anolyte compartment containing an anode and an electrolyte solution, a catholyte compartment containing a cathode, and an intermediate compartment containing a liquid, wherein said intermediate compartment is separated from the catholyte compartment by an anion selective membrane and from the anolyte compartment by a cation selective membrane, said process comprising the steps of:

(A) charging to the catholyte compartment, a mixture comprising an organic or inorganic salt or an amine salt, and a liquid selected from water or organic liquids provided that sufficient water is present in the catholyte mixture to form the desired hydroxide or amine, or sufficient alcohol is present in the catholyte mixture to form the desired alkoxide;

(B) passing a current through the electrolysis cell to produce the desired hydroxide, alkoxide or amine in the catholyte compartment and an acid in the intermediate compartment;

(D) recovering the organic or inorganic hydroxide or alkoxide or the amine from the catholyte compartment; and (E) recovering the acid from the intermediate compartment. The organic and inorganic hydroxides and alkoxides, or amines prepared by the process of the invention are characterized by improved purity, and production costs are lower than many other processes. The processes of the invention also are particularly useful for preparing higher molecular weight quaternary ammonium hydroxides and alkoxides.

DESCRIPTION OF THE PREFERRED EMBODIMENTS

Figure 1:
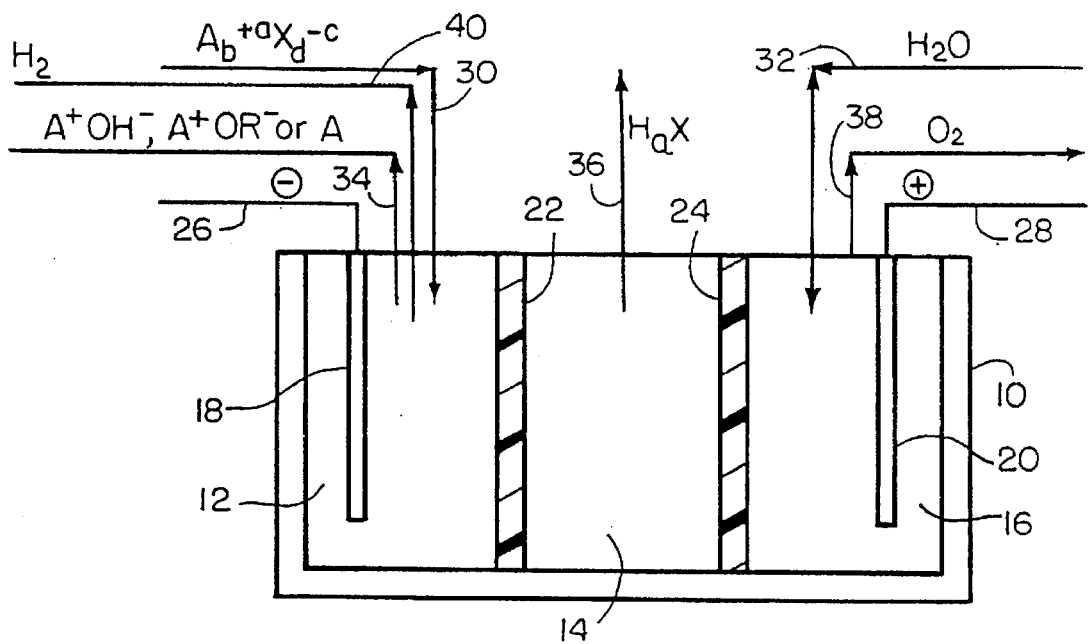
FIG. 1 is a schematic cross-section of an electrolytic cell useful in performing the processes of the invention.

In one embodiment, the process of the present invention involves the preparation of organic and inorganic hydroxides or alkoxides, or ammonia and organic amines from the corresponding organic and inorganic salts in an electrolysis cell. The salts may generally be characterized by the formula $$A_b^{+a} X_d^{-c} \tag{I}$$

wherein $A^+$ is an organic or inorganic cation, $X^-$ is an anion, a is a number equal to the valence of A, c is a number equal to the valence of X, and $a \times b = c \times d$ and wherein b and d are smallest numbers to satisfy the equation. Examples of anions include halogen ion, $HSO_4^-$, $CR_3COO^-$, $NO_3^-$, $BF_4^-$, $PF_6^-$, $R^1SO_3^-$, $SO_4^=$, $PO_4^=$, etc., where R is hydrogen or an alkyl or aryl group, and $R^1$ is an alkyl or aryl group. In one preferred embodiment $X^-$ is a halogen ion such as chloride, fluoride, bromide or iodide.

Examples of inorganic hydroxides and alkoxides which can be prepared from the corresponding salts, particularly from the halides, include the hydroxides and alkoxides of alkali metals such as sodium and potassium; alkaline earth metals such as magnesium and calcium; transition metals such as titanium, zirconium, chromium, manganese, iron, cobalt, nickel, copper, platinum; rare earth metals such as cerium, neodymium, samarium; etc. Specific examples of inorganic hydroxides which can be prepared in accordance with the process of the present invention include potassium hydroxide, magnesium hydroxide, ferric hydroxide, cuprous hydroxide, cupric hydroxide, cobaltous hydroxide, cobalitic hydroxide, etc. Although inorganic hydroxides may be prepared by the process of the invention, the hydroxides may be disproportination to the inorganic oxide and water. Examples of the various alkoxides include potassium methoxide, sodium ethoxide, etc. When the inorganic salt is soluble in water or alcohols or mixtures thereof, the mixture which is charged to the catholyte compartment is an aqueous, alcoholic or aqueous alcoholic solution of the metal salt, and when the metal salt is insoluble or at least partially insoluble in water or alcohols, the mixture which is charged to the catholyte compartment may be a suspension, dispersion or emulsion. The insolubles in the aqueous mixture contained in the catholyte compartment are maintained in suspension by agitation.

In another embodiment the process of the present invention involves preparing organic hydroxides and alkoxides such as quaternary ammonium hydroxides or alkoxides, quaternary phosphonium hydroxides or alkoxides, tertiary sulfonium hydroxides or alkoxides from the corresponding salts in an electrolytic cell. The salts may generally be characterized by the formula $$A_a^+ X^{-a} \tag{IA}$$

wherein $A^+$ is a quaternary ammonium, quaternary phosphonium or tertiary sulfonium cation, $X^-$ is an anion, and a is a number equal to the valence of X.

The quaternary ammonium and quaternary phosphonium salts may be characterized by the formula $$\left[ \begin{array}{c} R^4 \\ | \\ R^1 - A - R^3 \\ | \\ R^2 \end{array} \right]_a^+ X^{-a} \tag{II}$$

wherein A is a nitrogen or phosphorus atom, X and a are as described above in Formula I and $R^1$, $R^2$, $R^3$ and $R^4$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R^1$ and $R^2$ together with A may form a heterocyclic group provided that if the heterocyclic group contains a C=A group, $R^3$ is the second bond.

The alkyl groups may be linear or branched, and specific examples of alkyl groups containing from 1 to 20 carbon atoms include methyl, ethyl, propyl, butyl, pentyl, hexyl, heptyl, octyl, isooctyl, nonyl, decyl, isodecyl, dodecyl, tridecyl, isotridecyl, hexadecyl and octadecyl groups. $R^1$, $R^2$, $R^3$ and $R^4$ also may be hydroxyalkyl groups such as hydroxyethyl and the various isomers of hydroxypropyl, hydroxybutyl, hydroxypentyl, etc. In one preferred embodiment, the R groups are independently alkyl groups containing one to ten carbon atoms and hydroxyalkyl groups containing from two to three carbon atoms. Specific examples of alkoxyalkyl groups include ethoxyethyl, butoxymethyl, butoxybutyl, etc. Examples of various aryl and hydroxyaryl groups include phenyl, benzyl, tolyl, and equivalent groups wherein benzene rings have been substituted with one or more hydroxy groups.

Examples of quaternary ammonium salts representative of Formula II which can be treated in accordance with the process of the present invention to form quaternary ammonium hydroxides or alkoxides include tetramethylammonium chloride, tetramethylammonium bromide, bis-tetramethylammonium sulfate, tetraethylammonium chloride, tetraethylammonium bromide, tetraethylammonium nitrate, tetraethylammonium formate, tetraethylammonium acetate, tetrapropylammonium bromide, tetrabutylammonium bromide, tetra-n-octylammonium bromide, trimethylhydroxyethylammoniumchloride, trimethylmethoxyethylammoniumehloride, dimethyldihydroxyethylammonium chloride, methyltrihydroxyethylammonium chloride, phenyltrimethylammonium chloride, phenyltriethylammonium chloride, benzyltrimethylammoniumchloride, benzyltriethylammonium chloride, dimethylpyrolidinium bromide, dimethylpiperidinium bromide, diisopropylimidazolinium bromide, N-alkylpyridinium bromide, etc.

Examples of quaternary phosphonium salts representative of Formula II which can be treated in accordance with the process of the present invention to form quaternary phosphonium hydroxides or alkoxides include tetramethylphosphonium bromide, tetraethylphosphonium bromide, tetraethylphosphonium chloride, tetramethylphosphonium nitrate, tetramethylphosphonium acetate, tetrapropylphosphonium bromide, tetrabutylphosphonium bromide, trimethylhydroxyethylphosphonium bromide, dimethyldihydroxyethylphosphonium bromide, methyltrihydroxyethylphosphonium bromide, phenyltrimethylphosphonium bromide, phenyltriethylphosphonium bromide and benzyltrimethylphosphonium bromide.

Although Formulae I, IA and II illustrate organic quaternary ammonium and phosphorus compounds containing one nitrogen atom or one phosphorus atom, the present invention also contemplates the preparation of bis-quaternary ammonium and phosphonium compounds. Bis-quaternary ammonium hydroxides and alkoxides can be prepared from the corresponding bis-quaternary ammonium salt. For example

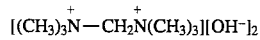

can be prepared from the corresponding halide salts.

In another embodiment, the tertiary sulfonium salts which can be treated in accordance with this invention to form tertiary sulfonium hydroxides or alkoxides may be represented by the formula

wherein a is a number equal to the valence of X, X is an anion as described above, particularly a halide ion, and $R^1$, $R^2$ and $R^3$ are each independently alkyl groups containing from 1 to about 20 carbon atoms, hydroxy alkyl or alkoxy alkyl groups containing from 2 to about 20 carbon atoms, aryl groups, or hydroxy aryl groups, or $R_1$ and $R_2$ together with S may form a heterocyclic group provided that if the heterocyclic group contains a C=S group, $R_3$ is the second bond.

Examples of the salts represented by Formula III include trimethylsulfonium chloride, trimethylsulfonium bromide, trimethylsulfonium nitrate, trimethylsulfonium acetate, triethylsulfonium bromide, tripropylsulfonium bromide, etc.

In another embodiment, ammonia and organic amines can be prepared by the process of the present invention from amine salts other than the quaternary ammonium salts described above. The electrolytic reaction which occurs in the catholyte compartment is essentially a neutralization reaction which can be represented as follows:

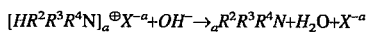

The union $X^{-a}$ migrates from the catholyte compartment to the intermediate compartment where it combines with a hydrogen ion to form an acid $H_aX$ where a is a number equal to the valence of X. The amine salts represented by the general formula

may be derived from ammonia or primary, secondary or tertiary amines. That is, $R^2$, $R^3$ and $R^4$ are each independently hydrogen, or alkyl groups containing from 1 to about 20 carbon atoms, or aryl groups containing from 6 to about 26 carbon atoms. The union $X^-$ may be any of the anions specified above. Preferably $X^-$ is a halide union. Examples of amine salts (IV) include ammonium chloride, methylammonium chloride, dimethylammonium chloride, triethylammonium bromide, methylethylammonium chloride, etc.

Mixtures comprising the organic or inorganic salts and water or an organic liquid, are charged to the catholyte compartment in the process of the invention. The mixtures may be solutions, suspensions, dispersions or emulsions. Preferably the mixtures are solutions containing water-soluble halide salts. The mixtures charged to the catholyte may contain from 3 to about 60% by weight or more of the salts.

The liquid which is present in the mixture charged to the catholyte compartment (i.e., the catholyte mixture) may be selected from water and organic liquids. Examples of such organic liquids include hydrocarbons, alcohols, ethers, etc., or mixtures thereof. However, during electrolysis, the liquid in the catholyte compartment should comprise sufficient water or alcohol to form the desired hydroxide or alkoxide. More specific examples of liquids which may be used include water, methanol, ethanol, propanol, ethylene glycol, diethylene glycol, hexane, heptane, benzene, toluene, xylene, etc. The mixture charged to the catholyte should not contain significant amounts of any other liquid which can react with a hydroxyl group or with the desired amine product unless this reaction forms a different desired product. Examples of such organic liquids which should be avoided in the catholyte mixture include acids, esters, ketones, aldehydes, amides, nitriles, etc. In one embodiment, it is preferred to avoid any liquid in the catholyte mixture in which the desired hydroxide, alkoxide or amine product is insoluble.

The liquid which is included in the mixture charged to the intermediate compartment may be water, an organic liquid, a mixture of water and organic liquids or mixtures of organic liquids. Almost any organic liquid may be used provided it does not interfere with the desired reaction in the intermediate compartment, namely, $H^+ + X^{-a} = H_aX$). Examples of organic liquids include alcohols such as methanol, ethanol, propanol, ethylene glycol, etc.; liquid hydrocarbons such as hexane, heptane, benzene, toluene, xylene, etc.; liquid ethers such as diethylene glycol and triethylene glycol. Water and alcohols are preferred liquids and water is the most preferred. Generally the liquid added to the intermediate compartment will contain a small amount of an acid. Preferably, the acid will be the same as the acid formed in the intermediate compartment during electrolysis. For example, if the salt in the catholyte compartment is a chloride, the acid originally added to the intermediate compartment is hydrochloric acid; if the salt is a nitrate, the acid is nitric acid; etc. Original acid concentrations in the intermediate compartment of about 0.1M are useful.

The liquid charged to the anolyte compartment is an electrolyte and is preferably an aqueous solution containing a small amount (e.g., about 1M) of an acid such as hydrochloric acid, nitric acid, sulfuric acid, etc. The liquid may be a mixture of water or alcohol, and one or more organic liquids such as alcohols (e.g., methanol) or aromatic solvents such as benzene, toluene, etc.

The electrolysis cell utilized in the processes of the present invention comprises three compartments: an anolyte compartment containing an anode, a catholyte compartment containing a cathode, and an intermediate compartment. The catholyte compartment is separated from the intermediate compartment by an anion selective membrane, and the anolyte compartment is separated from the intermediate compartment by cation selective membrane. The type of electrolysis cell used in the processes of the present invention may be any of the known electrolysis cells, and the cells may be composed of conventional cell materials which are compatible with the materials being charged into or formed in the compartments of the cells.

Various materials which have been used as anodes in electrolysis cells can be included in the cells used in the above and other embodiments of the present invention provided they do not react with the solution added to the cells. For example, the anode may be made of high purity graphite or metals such as, for example, titanium-coated or clad electrodes, tantalum, zirconium, hafnium or alloys of the same. Generally, the anodes will have a non-passivable and catalytic film which may comprise metallic noble metals such as platinum, iridium, rhodium or alloys thereof, or a mixture of electroconductive oxides comprising at least one oxide or mixed oxides of a noble metal such as platinum, iridium, ruthenium, palladium or rhodium.

Various materials which have been used as cathodes in electrolytic cells can be included in the cells used in the above and other embodiments of the present invention. Cathode materials include nickel, iron, stainless steel, nickel plated titanium, etc. Preferably, the cathodes in electrolytic cells utilized in the process of the present invention comprise zinc, cadmium, nickel, tin, lead, copper, iron or titanium or alloys thereof, mercury or mercury amalgams. The term "alloy" is used in a broad sense and includes intimate mixtures of two or more metals as well as one metal coated onto another metal. The mercury amalgam cathodes include, for example, mercury on nickel, mercury on copper, mercury on cadmium, mercury on zinc, etc.

The cation selective membranes separating the intermediate compartment from the anolyte compartment may be any of those which have been used in the electrolysis of quaternary ammonium salts to quaternary ammonium hydroxides. Preferably, the cation-exchange membranes should comprise a highly durable material such as the membranes based on the fluorocarbon series, or from less expensive materials of the polystyrene or polypropylene series. Preferably, however, the cation selective membranes useful in the present invention include fluorinated membranes containing cation selective groups such as perfluorosulfonic acid and perfluorosulfonic acid/perfluorocarboxylic acid, perfluorocarbon polymer membranes such as sold by the E.I. duPont Nemours & Co. under the general trade designation "Nation." Other suitable cation selective membranes include styrene-divinyl benzene copolymer membranes containing cation selective groups such as sulfonate groups, carboxylate groups, etc. The preparation and structure of cation selective membranes are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various cation selective membranes which can be useful in the process of the present invention.

The membrane which is utilized in the present invention to separate the catholyte compartment from the intermediate compartment is an anion selective membrane or an anion exchange membrane. Any anion selective membrane may be utilized including membranes used in processes for the desalination of brackish water. Preferably, the membrane should be selected which is more selective with respect to particular anions present in the anolyte. The preparation and structure of anionic membranes also are described in the chapter entitled "Membrane Technology" in *Encyclopedia of Chemical Technology*, Kirk-Othmer, Third Ed., Vol. 15, pp. 92–131, Wiley & Sons, New York, 1985. These pages are hereby incorporated by reference for their disclosure of various anionic membranes which may be useful in the process of the present invention. An example of a strongly basic anion exchange resin which can be used for forming membranes is a polystyrene-divinylbenzene copolymer having as basic functional groups linked thereto, quaternary ammonium or amino groups.

Among the anion selective membranes which may be utilized and which are commercially available are the following: AMFLON, Series 310, based on fluorinated polymer substituted with quaternary ammonium groups produced by American Machine and Foundry Company; IONAC MA 3148, MA 3236 and MA 3475, based on polymer substituted with quaternary ammonium derived from heterogenous polyvinylchloride produced by Ritter-Pfaulder Corp., Permutit Division; Tosflex IE-SF 34 or IE-SA 48 made by Tosoh Corp. which is a membrane designed to be stable in alkaline media; NEOSEPTA AMH, NEOSEPTA AFN or NEOSEPTA ACLE-SP from Tokuyama Soda Co.; and Selemion AMV from Asahi Glass. In one embodiment, the Tosflex IE-SF 34 and NEOSEPTA AMH anion exchange membranes are preferred because of their stability in alkaline solutions such as the quaternary ammonium hydroxide solution which is formed in the electrolytic process of the invention.

A schematic cross-section or representation of a three compartment electrolysis cell useful in the processes of the present invention described above is shown in FIG. 1. In FIG. 1, the electrolytic cell 10 comprises an anolyte compartment 16, a catholyte compartment 12 and an intermediate compartment 14. The anolyte compartment 16 is separated from the intermediate compartment 14 by a cation selective membrane 24, and the catholyte compartment 12 is separated from the intermediate compartment 14 by an anion selective membrane 22. The anolyte compartment contains an anode 20 which is attached to the power supply (not shown) by wire 28. The catholyte compartment 12 contains a cathode 18 attached to a power supply (not shown) through wire 26. The anolyte mixture containing a salt $A_b^{+a}X_d^{-c}$ is charged to the catholyte compartment 12 as illustrated by line 30, and the anolyte comprising an electrolyte (e.g., a dilute mineral acid solution) is charged to the anolyte compartment as illustrated by line 32.

The intermediate compartment also contains a liquid which is generally an aqueous electrolyte (generally a dilute acid solution). Electrolysis results in the formation of the desired hydroxide, alkoxide or amine and hydrogen in the catholyte compartment and passage of the anion $(X^{-a})$ through the anion selective membrane 22 to the intermediate compartment 14. The hydrogen formed in the catholyte and is removed from the catholyte compartment as shown by line 40. In the anolyte compartment, hydrogen ions and oxygen are formed, the hydrogen ions pass through the cation selective membrane 24 into the intermediate compartment, and oxygen evolves from the anolyte compartment as indicated by line 38. An acid $(H_aX)$ is formed in the intermediate compartment and can be removed as indicated by line 36. The desired hydroxide, alkoxide or amine which is formed in the catholyte compartment can be recovered as indicated by line 34.

Electrolysis of the mixture containing the organic or inorganic salt or the amine salt is effected by impressing a current voltage (generally direct current) between the anode and the cathode with a current density of about 5 to about 250 A/ft$^2$, and more preferably at a current density of from about 25 to about 150 A/ft$^2$. Alternatively, the current density may be about 0.5–25 A/dm$^2$ or from about 2.5 to 15 A/dm$^2$. The current is applied to the cell for a period of time which is sufficient to result in the formation of the desired amount of the hydroxide or alkoxide in the catholyte. Circulation is effected by pumping and/or by gas evolution. In practice, such electrolysis cell can be operated batchwise or in a continuous operation.

The examples in the following table illustrate in general, different charges to the catholyte, intermediate and anolyte compartments and the products formed and recovered from each of these compartments based upon said charges. In the table, $A^+$ is as defined in Formula I above, and $R^2$, $R^3$ and $R^4$ are as defined above in Formula IV.

TABLE

| | Illustration Charges and Products | | |
|---|---|---|---|
| | Catholyte | Intermediate | Anolyte |
| Charge | $A^+Cl^- + H_2O$ | $H_2O$ | aq. |
| Product | $A^+OH^- + H_2$ | HCl | electrolyte O$_2$ |
| Charge | $A^+Br^- + H_2O$ | $H_2O$ | aq. |
| Product | $A^+OH^- + H_2$ | HBr | electrolyte O$_2$ |
| Charge | $A^+NO_3^- + H_2O$ | $H_2O$ | aq. |
| Product | $A^+OH^- + H_2$ | HNO$_3$ | electrolyte O$_2$ |

TABLE-continued

| | Illustration Charges and Products | | |
|---|---|---|---|
| | Catholyte | Intermediate | Anolyte |
| Charge | $A^{+HSO_4^-} + H_2O$ | $H_2O$ | aq. |
| Product | $A^+OH^- + H_2$ | H$_2$SO$_4$ | electrolyte O$_2$ |
| Charge | $A^+RSO_3^- + H_2O$ | $H_2O$ | aq. |
| Product | $A^+OH^- + H_2$ | RSO$_3$H | electrolyte O$_2$ |
| Charge | $A^{+-}OOCH_3 + H_2O$ | $H_2O$ | aq. |
| Product | $A^+OH^- + H_2$ | CH$_3$COOH | electrolyte O$_2$ |
| Charge | $HR^2R^3R^4N\oplus Cl^- + H_2O$ | $H_2O$ | aq. |
| Product | $R^2R^3R^4N + H_2$ | HCl | electrolyte O$_2$ |
| Charge | $A^+Cl^- + H_2O + CH_3OH$ | $H_2O$ | aq. |
| Product | $A^{+-}OCH_3 + H_2$ | HCl | electrolyte O$_2$ |
| Charge | $A^+Br^- + H_2O + C_2H_5OH$ | $H_2O$ | aq. |
| Product | $A^{+-}OC_2H_5 + H_2$ | HBr | electrolyte O$_2$ |
| Charge | $A^+{}_2SO_4^= + H_2O$ | $H_2O$ | aq. |
| Product | $A^+OH^- + H_2$ | H$_2$SO$_4$ | electrolyte O$_2$ |

The following specific examples further illustrate the process of the present invention. Unless otherwise indicated in the following examples and elsewhere in the specification and claims, all parts and percentages are by weight, all temperatures are in degrees Centigrade, and pressure is at or near atmospheric pressure.

EXAMPLE 1

In this example, tetra-n-propylammonium hydroxide is prepared from tetra-n-propylammonium bromide. A three-compartment electrolysis cell is prepared containing a titanium anode coated with ruthenium oxide (8.4 in$^2$ or 5.8×10$^{-2}$ft$^2$) a nickel cathode (8.4 in$^2$ or 5.8×10$^{-2}$ft$^2$) an anion-selective membrane (Neosepta AMH, a Tokuyama Soda Co.), and a cation-selective membrane (Nation 423 from DuPont). The membranes are positioned in the cell such that the anion-selective membrane is faced to the cathode side while the cation-selective membrane is faced to the anode side. The two membranes are separated by means of a 0.5-inch thick polypropylene divider. A solution of 425 ml. of 1.0M tetra-n-propylammonium bromide is charged to the catholyte compartment. The intermediate compartment is charged with 560 ml. of 0.1M hydrobromic acid solution while 425 ml. of 0.98M sulfuric acid solution is introduced into the anolyte compartment. The electrolysis is carded out at 3.0 amp (50 A/ft$^2$) and a cell voltage of 8.0 volts. Deionized water is constantly added to both the catholyte and anolyte compartments to maintain a constant volume. After approximately 50 hours of electrolysis, a solution of 1.0M tetra-n-propylammonium hydroxide containing 258 ppm bromide is obtained in the catholyte compartment. An overall current efficiency of 8.8% is obtained.

EXAMPLE 2

The procedure of Example 1 is repeated except that the anolyte compartment is charged with a solution of 425 ml. of 0.24M sulfuric acid. The electrolysis is carded out at 3.0 amp (50 A/ft$^2$) and a cell voltage of 7.75 volts. After 42 hours of electrolysis, a solution of 1.0 M tetra-n-propylammonium hydroxide containing 360 ppm of bromide is obtained in the catholyte compartment. A cumulative current deficiency of 10.5% is achieved.

EXAMPLE 3

The general procedure of Example 1 is repeated except that the catholyte compartment is charged with a solution of 425 ml. of 1.0M tetra-n-butylammonium bromide. The electrolysis is carried out at 3.0 amps (50 A/ft$^2$) and a cell voltage of 8.0 volts. After 46 hours of electrolysis, a solution of 1.0M tetra-n-butylammonium hydroxide with 420 ppm bromide is obtained. A cumulative current efficiency of 12% is achieved.

EXAMPLE 4

The general procedure of Example 1 is repeated except that the catholyte compartment is charged with 425 ml. of a 1.0M solution of tetra-n-butylammonium chloride while 560 ml. of 0.1M hydrochloric acid solution is introduced into the middle compartment. The electrolysis is carried out at 3.0 amps (50 A/ft$^2$) and a cell voltage of 8.0 volts. After 44 hours of electrolysis, a solution of 1.0M tetra-n-butylammonium hydroxide containing 260 ppm of chloride is obtained. A cumulative current efficiency of 13% is achieved.

EXAMPLE 5

The general procedure of Example 1 is repeated except that the catholyte is charged with 425 ml. of 1.0M sodium based toluenesulfonate while the middle compartment is charged with 560 ml. of 0.1M toluenesulfonic acid solution. The electrolysis is carried out at 3.0 amps (50 A/ft$^2$) and a cell voltage of 6 volts. After the completion of electrolysis, sodium hydroxide is recovered from the catholyte compartment and 940 ml. of a 0.47M solution of toluene sulfonic acid is recovered from the middle compartment.

EXAMPLE 6

The general procedure of Example 1 is repeated except that the catholyte is charged with 425 ml. of a 1.0M solution of sodium hexane sulfonate, and the middle compartment is charged with 560 ml. of a 0.1M solution of hexane sulfonic acid. After completion of the electrolysis, sodium hydroxide is recovered from the catholyte compartment and the hexanesulfonic acid solution is recovered from the middle compartment.

EXAMPLE 7

The general procedure of Example 1 is repeated except that the catholyte is charged with 425 ml. of a 1.0M solution of sodium dodecanesulfonate, and the middle compartment is charged with 560 ml. of a 0.1M solution of dodecanesulfonic acid. After completion of the electrolysis, sodium hydroxide is recovered from the catholyte, and a dodecanesulfonic acid solution is recovered from the middle compartment.

The process of the present invention provides a method for preparing organic and inorganic hydroxides or alkoxides or ammonia or organic amines in water or organic solvents from the corresponding salts at reduced cost and improved purity. In addition, almost any type of anion selective membrane can be used for all of the salts independent of the nature and molecular weight of the cation since it is the anion (X$^-$) which migrates, not the bulky cation. Thus, it is possible, for example, to prepare a variety of tetraalkylammonium and phosphonium hydroxides or trialkyl sulfonium hydroxides using one apparatus and one type of membrane. The electrolysis can be conducted in such a manner and for a period of time which is sufficient to insure that substantially all of the anions migrate to the anolyte compartment which increases the purity of the hydroxide obtained in the catholyte compartment. Another advantage of the process of the present invention is the ability to utilize weakly acid solutions in the anolyte thus reducing corrosion and degradation of the materials of construction.

While the invention has been explained in relation to its preferred embodiments, it is to be understood that various modifications thereof will become apparent to those skilled in the art upon reading the specification. Therefore, it is to be understood that the invention disclosed herein is intended to cover such modifications as fall within the scope of the appended claims.

We claim:

1. A process for preparing organic and inorganic hydroxides or alkoxides, or ammonia and organic amines from the corresponding salts in an electrolysis cell which comprises an anolyte compartment containing an anode and an electrolyte solution, a catholyte compartment containing a cathode, and an intermediate compartment containing a liquid, wherein the intermediate compartment is separated from the catholyte compartment by an anion selective membrane and from the anolyte compartment by a cation selective membrane, said process comprising the steps of:

(A) charging to the catholyte compartment, a mixture comprising an organic or inorganic salt or an amine salt, and a liquid selected from water or organic liquids provided that sufficient water is present in the catholyte mixture to form the desired hydroxide or amine, or sufficient alcohol is present in the catholyte mixture to form the desired alkoxide or amine;

(B) passing a current through the electrolysis cell to produce the desired hydroxide, alkoxide or amine in the catholyte compartment and an acid in the intermediate compartment;

(D) recovering the organic or inorganic hydroxide or alkoxide or the amine from the catholyte compartment; and (E) recovering the acid from the intermediate compartment.

2. The process of claim 1 wherein the mixture charged to the catholyte compartment comprises sufficient water to form the desired organic or inorganic hydroxide or amine.

3. The process of claim 1 wherein the mixture charged to the catholyte compartment comprises sufficient alcohol to form the desired organic or inorganic alkoxide or amine.

4. The process of claim 1 wherein the salt charged to the catholyte compartment is characterized by the formula $$A_b^{+a} X_d^{-c} \qquad (I)$$

wherein A$^+$ is an organic or inorganic cation, X$^-$ is an anion, a is a number equal to the valence of A, c is a number equal to the valence of X and a×b=c×d wherein b and d are reduced to their lowest whole numbers.

5. The process of claim 4 wherein the anion is a halide anion.

6. The process of claim 4 wherein A$^+$ is a quaternary ammonium, quaternary phosphonium, tertiary sulfonium or an ammonium cation other than a quaternary ammonium cation.

7. The process of claim 4 wherein the salt is a quaternary ammonium, or quaternary phosphonium salt represented by the formula

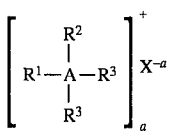

$$\left[\begin{array}{c} R^2 \\ | \\ R^1-A-R^3 \\ | \\ R^3 \end{array}\right]_a^+ X^{-a} \quad \text{(II)}$$

wherein A is nitrogen or phosphorus, X⁻ is an anion, a is a number equal to the valence of X, and $R^1$, $R^2$, $R^3$ and $R^4$ are each independently alkyl groups containing from 1 to about 20 carbon atoms, hydroxy alkyl or alkoxy alkyl groups containing from 2 to about 20 carbon atoms, aryl groups or hydroxy aryl groups, or $R^1$ and $R^2$ together with A may form a heterocyclic group provided that if the heterocyclic group contains a C=A group, $R^3$ is the second bond.

8. The process of claim 7 wherein $R^1$, $R^2$, $R^3$ and $R^4$ are each independently alkyl groups containing from 1 to about 20 carbon atoms.

9. The process of claim 4 wherein the salt is a tertiary sulfonium salt characterized by the formula

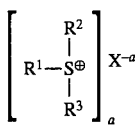

$$\left[\begin{array}{c} R^2 \\ | \\ R^1-S^{\oplus} \\ | \\ R^3 \end{array}\right]_a X^{-a} \quad \text{(III)}$$

wherein X⁻ is an anion, a is a number equal to the valence of X, $R^1$, $R^2$ and $R^3$ are each independently alkyl groups containing from 1 to about 20 carbon atoms, hydroxy alkyl or alkoxy alkyl groups containing from 2 to about 20 carbon atoms, aryl groups or hydroxy aryl groups, or $R^1$ and $R^2$ together with S may form a heterocyclic group provided that if the heterocyclic group contains a C=S group, $R^3$ is the second bond.

10. The process of claim 4 wherein $A^+X^-$ is an ammonium salt characterized by the formula

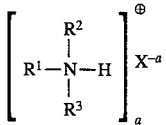

$$\left[\begin{array}{c} R^2 \\ | \\ R^1-N-H \\ | \\ R^3 \end{array}\right]_a^{\oplus} X^{-a} \quad \text{(IV)}$$

wherein X⁻ is an anion, a is a number equal to the valence of X, $R^1$, $R^2$ and $R^3$ are each independently hydrogen, alkyl groups containing from 1 to about 20 carbon atoms, hydroxy alkyl or alkoxy alkyl groups containing from 2 to about 20 carbon atoms, aryl groups, or hydroxy aryl groups, or $R^1$ and $R^2$ together with N may form a heterocyclic group provided that if the heterocyclic group contains a C=N, $R^3$ is the second bond.

11. A process for preparing organic and inorganic hydroxides from the corresponding halide salt in an electrolysis cell which comprises an anolyte compartment containing an anode and an aqueous acidic mixture, a catholyte compartment containing a cathode, and an intermediate compartment containing an aqueous acid mixture wherein the intermediate compartment is separated from the catholyte compartment by an anion selective membrane, and from the anolyte compartment by a cation selective membrane, said process comprising the steps of (A) charging to the catholyte compartment an aqueous mixture containing an organic or inorganic halide salt;

(B) passing a current through the electrolysis cell to produce the organic or inorganic hydroxide in the catholyte compartment and an inorganic acid in the intermediate compartment;

(C) recovering the organic or inorganic hydroxide from the catholyte compartment; and (D) recovering the inorganic acid from the intermediate compartment.

12. The process of claim 11 wherein the halide salt charged to the catholyte compartment is an organic halide salt characterized by the formula $$A^+X^- \quad \text{(I)}$$

wherein $A^+$ is an organic cation, and X⁻ is a halide anion.

13. The process of claim 12 wherein the halide is a bromide or chloride.

14. The process of claim 11 wherein the organic or inorganic halide salt charged to the catholyte compartment is a quaternary ammonium, quaternary phosphonium or tertiary sulfonium halide salt.

15. The process of claim 11 wherein the halide salt charged to the catholyte compartment is a quaternary ammonium halide salt.

16. A process for preparing quaternary ammonium hydroxides from quaternary ammonium halides in an electrolysis cell which comprises an anolyte compartment containing an anode and an aqueous acidic mixture, a catholyte compartment containing a cathode, and an intermediate compartment containing an aqueous acidic mixture wherein the intermediate compartment is separated from the catholyte compartment by an anion selective membrane and from the anolyte compartment by a cation selective membrane, said process comprising the steps of:

(A) charging to the catholyte compartment, an aqueous solution containing a quaternary ammonium halide characterized by the formula

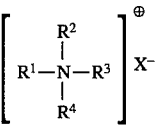

$$\left[\begin{array}{c} R^2 \\ | \\ R^1-N-R^3 \\ | \\ R^4 \end{array}\right]^{\oplus} X^- \quad \text{(II)}$$

s wherein $R^1$, $R^2$, $R^3$ and $R^4$ are each independently alkyl or hydroxy alkyl groups containing from 3 to about 20 carbon atoms, and X is bromide or chloride;

(B) subjecting the mixtures in the catholyte, anolyte and intermediate compartments to electrolysis by passing a current through the electrolysis cell to form a quaternary ammonium hydroxide in the catholyte compartment and an inorganic acid in the intermediate compartment;

(C) recovering the quaternary ammonium hydroxide from the catholyte compartment; and (D) recovering the inorganic acid from the intermediate compartment.

17. The process of claim 16 wherein $R^1$, $R^2$, $R^3$ and $R^4$ in Formula II are each independently alkyl groups containing from 3 to about 20 carbon atoms.

18. The process of claim 16 wherein $R^1$, $R^2$, $R^3$ and $R^4$ in Formula II are each independently alkyl groups containing from 3 to about 10 carbon atoms.

19. The process of claim 16 wherein $R^1$, $R^2$, $R^3$ and $R^4$ in Formula II are each independently propyl or butyl groups.

20. The process of claim 16 wherein the concentration of quaternary ammonium halide in the aqueous solution charged in step (A) is from about 3% to about 60% by weight.

21. The process of claim 16 wherein X is bromide.

22. A process for preparing inorganic hydroxides from inorganic salts in an electrolysis cell which comprises an anolyte compartment containing an anode and an aqueous acidic mixture, a catholyte compartment containing a cathode, and an intermediate compartment containing an aqueous acidic mixture and which is separated from the catholyte compartment by an anion selective membrane and is separated from the anolyte compartment by cation selective membrane, said process comprising the steps of:

(A) charging to the catholyte compartment, an aqueous mixture comprising an inorganic salt;

(B) passing a current through the electrolysis cell to produce the inorganic hydroxide in the catholyte compartment and additional acid in the intermediate compartment;

(C) recovering the inorganic hydroxide from the catholyte compartment; and (D) recovering the acid from the intermediate compartment.

23. The process of claim 22 wherein the inorganic salt charged to the catholyte compartment is selected from alkali metal halides, sulfates, sulfonates and phosphates.

24. The process of claim 22 wherein the inorganic salt charged to the catholyte compartment is an alkali metal alkyl sulfonate, and the aqueous acidic mixture initially in the intermediate compartment is an aqueous solution of an alkyl or aryl sulfonic acid.

25. A process of preparing amines or ammonia from the corresponding ammonium salts in an electrolysis cell which comprises an anolyte compartment containing an anode and an aqueous acidic mixture, a catholyte compartment containing a cathode, and an intermediate compartment containing an aqueous acidic mixture and which is separated from the catholyte compartment by an anion selective membrane and separated from the anolyte compartment by a cation selective membrane, said process comprising the steps of:

(A) charging to the catholyte compartment, an aqueous solution comprising an ammonium salt;

(B) passing a current through the electrolysis cell to produce the amine in the catholyte compartment and an acid in the intermediate compartment;

(C) recovering the amine from the catholyte compartment; and (D) recovering the acid from the intermediate compartment.

26. The process of claim 25 wherein the amine salt charged to the catholyte compartment is characterized by the formula

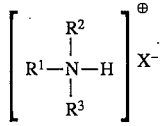  (IV)

wherein $R^1$, $R^2$ and $R^3$ are each independently hydrogen, alkyl groups containing from 1 to about 10 carbon atoms, hydroxy alkyl or alkoxy alkyl groups containing from 2 to about 10 carbon atoms, aryl groups, or hydroxy aryl groups, and X is a halide.

27. The process of claim 26 wherein X is a chloride or a bromide.

28. The process of claim 26 wherein X is bromide, and hydrogen bromide is recovered from the intermediate compartment.

29. The process of claim 26 wherein R, $R^2$ and $R^3$ are each independently alkyl groups.

* * * * *